United States Patent [19]
Strauss

[11] 4,344,425
[45] Aug. 17, 1982

[54] EARPLUGS

[76] Inventor: Richard H. Strauss, 1501 Doone Rd., Columbus, Ohio 43221

[21] Appl. No.: 158,276

[22] Filed: Jun. 10, 1980

[51] Int. Cl.³ ............................................. A61F 11/02
[52] U.S. Cl. ................................................... 128/152
[58] Field of Search ................ 128/151, 152, 153, 156

[56] References Cited
U.S. PATENT DOCUMENTS 2,574,288  11/1951  Rosenblatt .......................... 128/152
2,716,625  8/1955   Scholl ................................. 128/153
3,487,832  1/1970   Spence ............................... 128/153

Primary Examiner—Henry J. Recla
Attorney, Agent, or Firm—Cushman, Darby & Cushman

[57] ABSTRACT

A protective plug for sealing the ear canal has a tacky adhesive surface which when pressed against the skin attaches the plug temporarily in place. Retention of the plug does not rely on friction developed by compression of the body of the plug as it is inserted in the ear canal, and therefore the plug need not fit tightly into the ear canal and in some cases the plug may merely overlie the mouth of the canal. The adhesive surface may be a layer of adhesive applied to a substrate or it may be the surface of a body of plug material which is inherently tacky. The plug can be modified to transmit sound well while excluding water or to minimize sound transmission.

6 Claims, 16 Drawing Figures

EARPLUGS

PRIOR ART

Earplugs are used to prevent entry of foreign material, especially water, into the ear canal. They are also used to prevent or reduce entry of sound waves, thereby providing auditory protection or assisting the wearer in sleeping. Such plugs are usually designed to fit into the ear canal to be engaged more or less tightly by the wall of the canal inside the entrance area thereof to frictionally hold the plug in place. They remain in place because they are wedged into the ear canal, and they tend to leak, fall out or irritate the canal because of the wedge pressure.

In addition to these well known types of rubber or foamed plastic plugs that are designed for frictionally engaging the walls of the canal, there are other kinds of plugs such as one made of a putty-like silicone resin body shaped into a form for insertion into the canal to form an earplug, the resin being encased in a flexible envelope to aid its insertion into the canal where it likewise is held in place by frictional engagement with the wall of the canal. This type of earplug is described in U.S. Pat. No. 3,771,521.

Another somewhat similar plug is shown in U.S. Pat. No. 4,160,449, where a foam plastic encased in a thin flexible envelope is utilized to hold the foam compressed during insertion into the canal, the compressed foam being released upon insertion in the canal to expand and engage the wall of the canal.

As an alternative to a plug engaged within the ear canal, U.S. Pat. No. 4,134,153 discloses a bag-like structure for enclosing the entire ear. The bag is attached to the head with a pressure sensitive adhesive.

All of these known means have defects in use and are either uncomfortable to wear over long periods of time or do not, in the case of the bag-type seal, provide a very effective seal. Swimmers may move through the water rapidly or may be subjected to rough treatment by breakers during ocean bathing and such vigorous water action may wash away frictionally held plugs or the bag-type of ear enclosure. Further, if the more popular frictionally supported plugs are used during periods of highly active swimming and diving for example, the plugs must be tightly engaged in the ear canal and soon become very uncomfortable to wear.

BRIEF DESCRIPTION OF THIS INVENTION

The present invention provides an earplug having an adhesive skin-engaging surface for releasably attaching the plug to the ear and for forming a seal with the skin. In its broadest application the invention contemplates any existing earplug having such an adhesive surface. In the preferred construction the plug does not rely on friction developed by compression of the plug body as it is inserted into the ear canal, and therefore the plug need not fit tightly into the canal. The plug therefore is comfortable when worn for long periods of time and does not irritate the ear canal. In some embodiments the plug may actually overlie the ear canal, rather than being inserted into the canal. In either case the adhesive surface engages the mouth of the ear canal and forms a seal therewith sufficient to prevent entry of foreign material and/or sound waves and sufficient to hold the plug in place even during, for example, surf bathing.

The adhesive surface of the plug may be a layer of adhesive applied to a substrate, or it may be the surface of a body of plug material which is inherently tacky. Certain known silicone resin materials containing fillers are suitable as the plug material, the previously identified U.S. Pat. No. 3,771,521 disclosing one such material.

When the adhesive is an applied layer, the substrate may be a film or membrane, preferably pliable and stretchable so that it will easily conform to the ear canal opening. The film or membrane may initially be flat or may conveniently be initially concave-convex, for example, cup-shaped or frusto conical so that it generally fits a typical ear canal opening. Alternatively, the substrate may be made of somewhat thicker material such as a hollow or solid foam rubber body in the shape of a cone or frustum.

When the ear plug is made of inherently tacky, deformable, elastic material, it may be initially a flat circular or oval disc. To assure that the resin material will not stick to and remain on the skin when the plug is removed a coarse gauze layer may be incorporated in or on the skin-engaging surface of the plug. Alternatively, the resin may have incorporated into it a filler material to increase cohesive strength. A film of plastic or paper may be applied to the opposite surface of the disc to prevent sticking of the resin to the fingers during application and removal of the plug.

The invention also contemplates the provision of a sound window in an ear plug, to enable swimmers to hear when spoken to.

The invention also contemplates the use of a membrane or plug of increased mass in order to further reduce sound transmission for purposes of auditory protection or sleeping.

The invention also contemplates a packaging arrangement for throw-away ear plugs, the package itself having utility as a tool for use in inserting the adhesive plug in place.

IN THE DRAWINGS

DETAILED DESCRIPTION

Figure 1:
FIG. 1 is a sectional view of an ear plug embodying the principles of the present invention.
Figure 2:
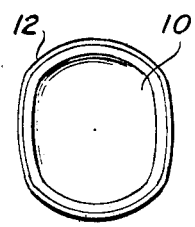
FIG. 2 is a back view of the plug shown in FIG. 1.
Figure 16:
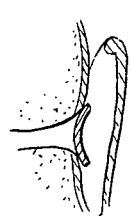
FIG. 16 shows a typical plug adhesively attached to the ear at the mouth of the auditory canal.

FIGS. 1 and 2 illustrate an earplug in the form of a deformable substrate 10 having on its front surface a layer of flexible, waterproof, pressure-sensitive adhesive 12. The plug can be shaped by light finger pressure to fit over the wearer's external acoustic meatus, or ear canal mouth, without extending substantially into the channel so that the plug can completely fill the mouth of the canal to seal it, as shown in FIG. 16. The substrate 10 may be a body of malleable plastic material, either foamed or unfoamed, or a thin pliable stretchable film or membrane. As shown the front surface of the plug is generally spherical, but this surface could also be cup-like, conical, frusto-conical or otherwise generally convex so that the plug initially tends to fit into the meatus. Prior to application, the earplug may even be flat. If the substrate is thin, as illustrated in FIGS. 1 and 2, the rear surface may be more or less complementary to the front surface. When the plug is gently pushed against the skin by the tip of the wearer's finger, the front surface of the plug becomes adhered around the entire periphery of the entrance to the canal to effectively seal it.

Any suitable pressure-sensitive adhesive such as is used on temporary bandages may be utilized and where the plug is to be used by swimmers, the adhesive is waterproof. The adhesive may also be a silicone resin with or without filler. The adhesive is pushed against the skin with a uniform pressure as the substrate 10 deforms to fit the plug intimately to the contours of the particular ear into which the plug is being fitted so that a secure and firm seal can be made.

Figure 6:
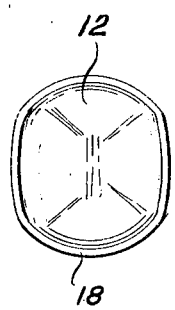
FIG. 6 is a front view of a third embodiment.
Figure 7:
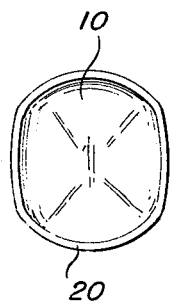
FIG. 7 is a back view of a fourth embodiment.

An inexpensive plug can be made from an adhesively coated elastic tape that can be deformed to fit the mouth of the ear canal. Rubber plugs, foamed plastic shapes and other plastic substances suggest themselves for this purpose. In view of the low cost of the materials the plug can be discarded after one use, so that a clean plug is always pressed into the ear.

Where the plug is to be used in situations where turbulent conditions may prevail around the ear, additional sealing means may be added around the periphery of the plug as shown in FIGS. 6 and 7. FIG. 6 illustrates the use of a ring of sealing adhesive such as a sticky silicone resin 18 applied to the periphery of the inner surface of the substrate. When such a plug is pressed against the mouth of the ear canal, the adhesive layer 12 seals the plug against the periphery of the mouth and the added ring 18 of the much tackier and deformable sealing material may be pressed against the skin to seal the edge of the plug against an outer portion of the ear beyond the mouth to the canal. As shown in FIG. 7, the added ring 20 of sealing material may be carried on the periphery of the plug on the outer surface thereof. After such a plug has been initially set in the ear, the tacky sealant 20 may be spread down around the plug's edge to more surely prevent leakage of water and to more surely seal the plug to the ear in a manner to preclude the possibility that any of the additional sealing material will get into the ear canal. This may be desirable since the added sealant preferably has a strong bonding characteristic selected for the very purpose of attaching itself to the surface to which it is applied in order to provide the stronger seal that may be needed to prevent the plug from being dislodged such as when the breakers pound against the head of a swimmer in the ocean surf.

Figure 8:
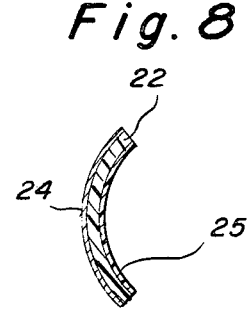
FIG. 8 is a sectional view of a fifth embodiment.

The plug shown in FIG. 8 is made of a moldable, pliant plastics material, such as a silicone resin with filler 22, which is itself sufficiently tacky to adhere to the skin and which therefore does not need a layer of adhesive thereon. In order to prevent such a resin from entering too far into the ear canal and to ensure that the resin will pull away from the skin when the plug is removed, the front surface of the plug is covered with a coarse gauze-like layer 24 as a reinforcement. When the plug is applied to the ear, the gauze layer is sealed under the plug with the adhesive resin touching the skin through the porous weave of the gauze and when the plug is removed, the gauze causes all of the silicone resin to be lifted from the skin surface as the plug is pulled free. The gauze must have a sufficient area of contact with the resin to keep it intact when the plug is pulled free but must have a somewhat open weave to permit the resin to freely contact the skin to which the plug is to be attached. A cheesecloth type gauze is appropriate for this purpose. The other side of such a plug as is shown in FIG. 8, may be covered with a plastic film 25 or the like to prevent the user's finger from sticking to the plug during handling. When a filler consisting of short fibers is added to silicone putty, the result is a tacky but cohesive material that can be formed into a thick membrane which alone can seal the ear canal yet can be removed with ease.

Figure 9:
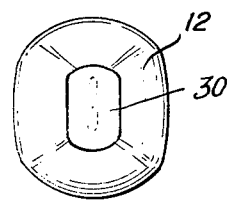
FIGS. 9 and 10 are a front view and a sectional view, respectively, of a sixth embodiment having a sound window therein.
Figure 10:
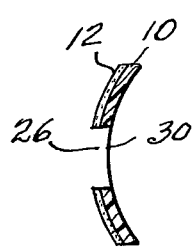
Figure 12:
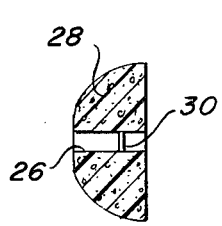
FIGS. 12 and 13 are a sectional view and a back view, respectively, of an earplug having a sound window therein.
Figure 13:
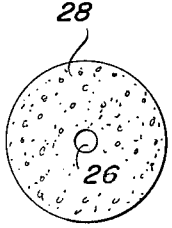

Industrial users of earplugs sometimes must be able to listen for certain sounds while having their ears sealed against entry of foreign substances. Also swimmers may wish to hear instructions called to them by a coach. Plugs can be made for such use and, as shown in FIGS. 9 and 10, the plug may be provided with a sound passage 26. A thin plastic membrane 30 is sealed around its periphery to the passage 26 to prevent the entry of water or dust. The membrane serves as a diaphragm which vibrates with sound waves to let sufficient sound energy pass to the inner ear as needed. Another embodiment is shown in FIGS. 12 and 13. The plug body 28 is provided with a sound passage 26 which is sealed by a thin plastic membrane 30. The plug 28 may be a conventional rubber or plastic plug held in place by friction, or it may be an adhesive plug as described above.

Figure 14:
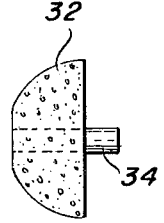
FIGS. 14 and 15 show a side elevation and end view of another form of the plug for cooperating with a hearing aid or earphone.
Figure 15:
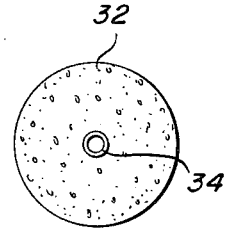

A somewhat similar plug is shown in FIGS. 14 and 15 where a foamed plastic plug 32 is shown fitted with a tube 34 adapted to be connected to a hearing aid or earphone device. The modern hearing aid may be made so light and small that the complete device may be mounted within the ear and held in place by a properly fitted earplug adhered to the mouth of the ear canal as described herein.

Figure 11:
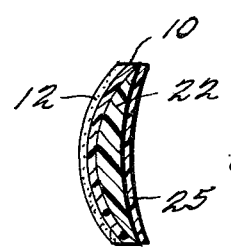
FIG. 11 is a sectional view of a seventh embodiment having additional mass in order to further decrease the transmission of sound waves.

Persons who must work or sleep in a noisy environment sometimes wish to minimize sound transmission to the ear. This can be accomplished particularly effectively through use of the earplug shown in FIG. 11 in which the substrate 10 and adhesive 12 are utilized as described previously. However, an additional layer of plastic material 22, such as silicone putty, is added to further diminish transmission of sound waves. A thin outer membrane of plastic film 25 may be added so that the material 22 does not adhere to the finger or to bedding during sleep.

The adhesive plugs of the invention plugs can be dispensed in cartons and can be made so inexpensively as to be disposable after use, and this is desirable for sanitary reasons. Also, the plugs can be distributed at such low cost as to encourage their use by all swimmers and others who might not find the previously known plugs satisfactory.

Figure 3:
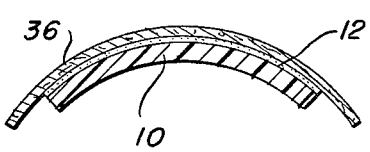
FIG. 3 is an enlarged cross-sectional view of a similar plug with a removable paper cover over the adhesive.
Figures 4, 5:
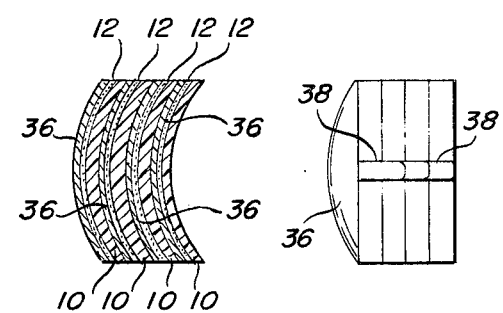
FIG. 4 is a sectional view of a stacking arrangement for a plurality of the plugs shown in FIG. 3.
FIG. 5 is a side view of the stack of plugs shown in FIG. 4.

A package for holding a plurality of plugs of the general kind shown in FIG. 3 is shown in FIGS. 4 and 5. When a generally conically shaped plug is made as shown in the enlarged view of FIG. 3, the plug body 10, which has a coating of adhesive 12 applied to its front surface, can be prepared for distribution by covering the tacky adhesive with a removable paper or plastic layer 36. The removable layer 36 has tabs 38 integral therewith as seen in FIG. 5 and a plurality of such plugs may be stacked together as shown in FIGS. 4 and 5, with the tabs 38 being used to bind the stack together by being lightly adhered on their back sides to the other plugs in the stacks of plugs.

When the stack of plugs is to be used, the layer 36 on the end plug in the stack, is removed to expose the adhesive face of that plug. The stack of plugs can then be used as a tool to position and press the exposed plug in an ear canal to seal it. The tabs 38, integral with layer 36, have been unstuck from the stack when layer 36 is removed so that the end plug has been released from the stack and after the plug is adhered to the ear when the stack is pulled away, the plug attached to the ear remains in the ear and the remaining plugs are retained in the stack. The plug that has been applied to the ear can now be pressed more firmly into sealing contact with the ear canal without fear of dirt from a finger entering the canal.

The preferred form of making and using the plug of this invention has been described above. It is possible that many types of materials other than those specifically mentioned herein may be found satisfactory for making the various forms of plugs for the several uses set forth above for this protective earplug. The plug may be conveniently supplied in various sizes for fitting differently sized ear structures as found in men, women and children. However, with the preferred structure, because of the deformability of the putty-like silicone resin selected, a plug of this design can be used quite satisfactorily to seal ears that vary greatly in size and individual configuration.

It is possible that many modifications of this invention will occur to those skilled in the art that may fall within the scope of the following claims.

What is claimed is:

1. An earplug comprised of a preformed concave-convex imperforate disc of pliable stretchable film of a size and shape such that the convex surface thereof is adapted to conform to and cover the opening of the ear canal and such that the disc is adapted to reside within the external ear when positioned over the ear canal opening, and a layer of pressure-sensitive adhesive on the convex surface for releasably adhering the disc to the periphery of the ear canal opening.

2. An earplug as in claim 1 wherein the adhesive is in the form of a ring on the periphery of the disc.

3. An earplug as in claim 2 wherein the adhesive is a silicone resin which can be spread outwardly from the periphery of the disc so as to be adhered to the skin around the ear canal opening.

4. An earplug comprised of a preformed concave-convex imperforate disc of deformable plastic material of a size and shape such that the convex surface thereof is adapted to conform to and cover the opening of the ear canal and such that the disc is adapted to reside within the external ear when positioned over the ear canal opening, and a layer of pressure-sensitive adhesive on the convex surface for releasably adhering the disc to the periphery of the ear canal opening.

5. An earplug as in claim 4 wherein the adhesive is in the form of a ring on the periphery of the disc.

6. An earplug as in claim 5 wherein the adhesive is a silicone resin which can be spread outwardly from the periphery of the disc so as to be adhered to the skin around the ear canal opening.

* * * * *